(12) United States Patent
Budman

(10) Patent No.: US 6,241,944 B1
(45) Date of Patent: Jun. 5, 2001

(54) AROMA SENSORY STIMULATION IN MULTIMEDIA AND METHOD FOR USING

(75) Inventor: Mark Budman, Vestal, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/421,908

(22) Filed: Oct. 20, 1999

Related U.S. Application Data

(63) Continuation of application No. 09/094,280, filed on Jun. 9, 1998, now Pat. No. 6,024,783.

(51) Int. Cl.[7] ............................................. A61L 9/00
(52) U.S. Cl. .................... 422/4; 96/222; 261/26; 261/104; 261/DIG. 17; 261/DIG. 65; 261/30; 422/1; 422/3; 422/5; 422/108; 422/109; 422/110; 422/116; 422/120; 422/123; 422/125
(58) Field of Search ........................... 422/120, 123, 422/125, 108, 109, 110, 116, 1, 5, 3, 4; 96/222; 261/26, 104, DIG. 17, DIG. 65, 30

(56) References Cited

U.S. PATENT DOCUMENTS

| | | |
|---|---|---|
| 3,585,991 | 6/1971 | Balamuth . |
| 4,556,539 | 12/1985 | Spector . |
| 4,603,030 | 7/1986 | McCarthy . |
| 4,629,604 | 12/1986 | Spector . |
| 4,647,433 | 3/1987 | Spector . |
| 4,695,434 | 9/1987 | Spector . |
| 4,771,344 | 9/1988 | Fallacaro et al. . |
| 5,071,621 | 12/1991 | Tokuhiro et al. . |
| 5,105,133 | 4/1992 | Yang . |
| 5,171,485 | 12/1992 | Ryan . |
| 5,297,988 | 3/1994 | Nishino et al. . |
| 5,318,503 | 6/1994 | Lord . |
| 5,398,070 | 3/1995 | Lee . |
| 5,565,148 | * 10/1996 | Pendergrass, Jr. ............. 261/30 |
| 5,577,668 | 11/1996 | King et al. . |
| 5,591,409 | 1/1997 | Watkins . |
| 5,724,256 | 3/1998 | Lee et al. . |
| 5,760,873 | * 6/1998 | Wittek ............................ 422/124 |
| 5,958,346 | * 9/1999 | Evans, Jr. ....................... 422/120 |
| 5,972,290 | * 10/1999 | De Sousa .......................... 422/5 |
| 6,024,783 | * 2/2000 | Budman ........................... 96/222 |

* cited by examiner

*Primary Examiner*—Krisanne Thornton
(74) *Attorney, Agent, or Firm*—Schmeiser, Olsen & Watts; John R. Pivnichny

(57) ABSTRACT

An apparatus for the remote or local delivery of stored or real-time aroma sensory information to an end user of a multimedia device. The present invention includes an aroma converter for encoding aroma information into electrical signals, a delivery system for delivering the electrical signals, and a retrieval system for receiving and processing the electrical signals to control the aroma or combination of aromas emitted by one or more aroma release chambers.

41 Claims, 2 Drawing Sheets

AROMA SENSORY STIMULATION IN MULTIMEDIA AND METHOD FOR USING

This is a continuation of patent application Ser. No. 09/094,280, filed Jun. 9, 1998, now U.S. Pat. No. 6,024,783.

FIELD OF THE INVENTION

The present invention is in the field of multimedia devices. More particularly, the present invention provides an apparatus for the delivery of aroma sensory information to a user of a multimedia device.

BACKGROUND OF THE INVENTION

Currently available multimedia devices, such as computers, video games, and televisions, are designed to provide visual and audio sensory information to a user. In many applications, however, it may be desirable to additionally provide aroma sensory information to enhance the realism and appeal of the information presented to a user by the multimedia device.

SUMMARY OF THE INVENTION

The present invention provides an apparatus for the remote or local delivery of stored or real-time aroma sensory information to an end user of a multimedia device. The present invention includes an aroma converter for encoding aroma information into electrical signals. The electrical signals may be delivered to an end user in analog or digital form using a wide variety of delivery systems, including, but not limited to, magnetic media (e.g., a floppy or hard disk), optical or magneto-optical media (e.g., a compact disc (CD)), radio, television, or satellite transmitters, or telephone or cable systems. The electrical signals are retrieved and processed to control the aroma or combination of aromas emitted by one or more aroma release chambers. Many types of retrieval systems may be used to receive and process the electrical signals. The retrieval system may include, for example, a personal computer or computer peripheral, a video game system, a television set, a home entertainment/theater system, or a dedicated, stand-alone module.

Generally, the present invention provides an apparatus for aroma sensory stimulation comprising:
an aroma converter for encoding aroma information into electrical signals;
a control device for processing the electrical signals; and
at least one aroma release chamber, each aroma release chamber configured to selectively generate a predetermined aroma under control of the control device, each aroma release chamber comprising:
a container having an opening;
a door for selectively covering the opening in the container;
an aroma element, located within the container, for emitting a predetermined aroma when heated;
a heating system for selectively heating the aroma element;
an air filtration system for filtering air entering the container; and
an air displacement system for selectively displacing a stream of air through the container to release the predetermined aroma.

BRIEF DESCRIPTION OF THE DRAWINGS

The features of the present invention will best be understood from a detailed description of the invention and a preferred embodiment thereof selected for the purposes of illustration and shown in the accompanying drawings in which.

DETAILED DESCRIPTION OF THE INVENTION

Figure 1:
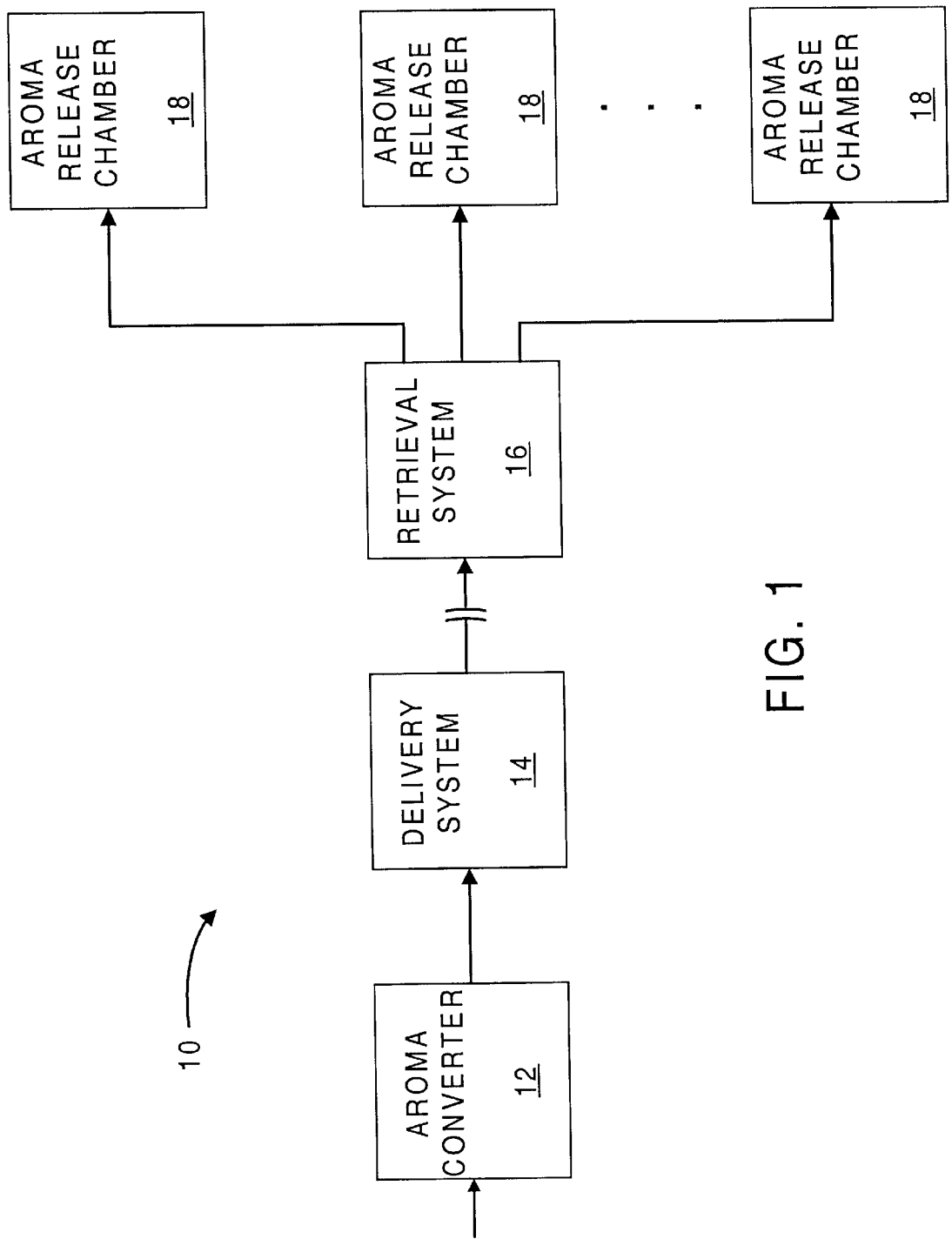
FIG. 1 illustrates a block diagram of an aroma sensory stimulation apparatus according to the present invention.

The features and advantages of the present invention are illustrated in detail in the accompanying drawings, wherein like reference numerals refer to like elements throughout the drawings.

A block diagram of an aroma sensory stimulation apparatus, generally designated as 10, according to the present invention, is illustrated in FIG. 1.

The aroma sensory stimulation apparatus 10 includes an aroma converter 12 for encoding aroma information into electrical signals. The aroma information may be converted into analog or digital electrical signals, depending on such factors as the type of delivery and retrieval systems to be used in a given implementation of the aroma sensory stimulation apparatus 10.

The aroma information may be encoded using a wide variety of techniques. For example, an aroma sensory stimulation apparatus 10 configured to produce sixteen (16) distinct aromas may encode the aroma information using a 4-bit digital word or sixteen distinct voltage levels. The scent of a rose, for example, may be encoded as "0001," while the aroma of a rotten egg may be encoded as "1111." An error correcting technique may be employed to ensure the correct delivery of the encoded aroma information.

The electrical signals produced by the aroma converter 12 are delivered to a local or remote end user in an analog or digital format by a delivery system 14. The delivery system 14 may take on a wide variety of forms. For example, the delivery system 14 may comprise a data carrier such as a floppy or hard disk, a compact disc, or other type of magnetic, optical or magneto-optical media, having the electrical signals saved or encoded thereon. Alternately, the delivery system may comprise a system for transmitting the electrical signals via radio, television, satellite, telephone, or the Internet.

A retrieval system 16 is provided to retrieve and process the electrical signals delivered by the delivery system 14 to control the aroma or combination of aromas emitted by one or more aroma release chambers 18. The retrieval system 16 may also take on a wide variety of forms, depending on the type of delivery system 14 being used, the format of the electrical signals provided by the delivery system 14, as well as other factors. For example, the retrieval system 16 may comprise a personal computer, a video game system, or a television set. It should be clear, however, that many other types of delivery and retrieval systems 14, 16 may be used without departing from the intended scope of the present invention as set forth in the accompanying claims.

Figure 2:
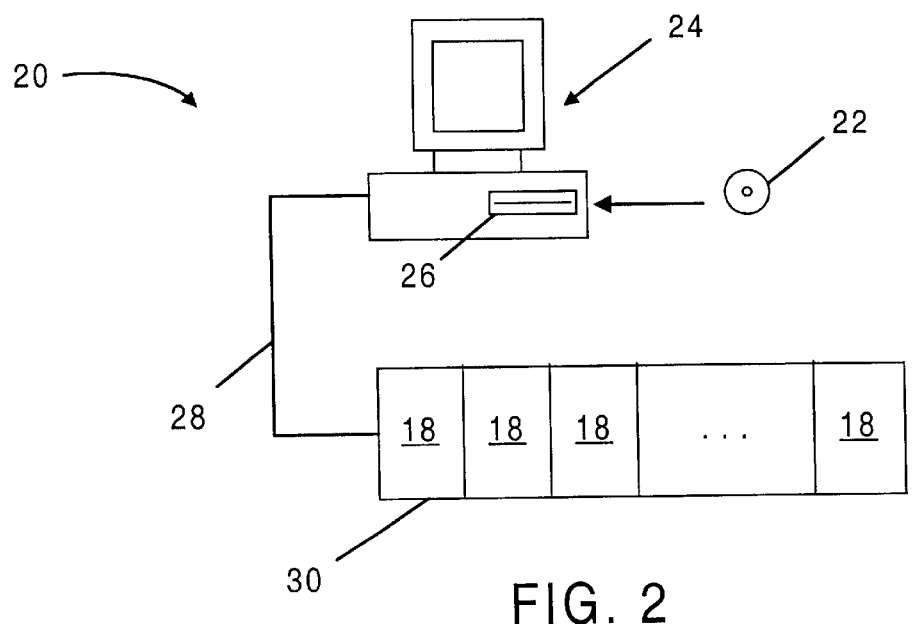
FIG. 2 illustrates an aroma sensory stimulation apparatus according to a preferred embodiment of the present invention.

An aroma sensory stimulation apparatus 20 according to a preferred embodiment of the present invention is illustrated in FIG. 2. In this embodiment, the delivery system comprises a compact disc 22 having aroma information encoded thereon. A computer system 24 including a compact disc reader 26 serves as the retrieval system for accessing and processing the aroma information stored on the compact disc 22. The computer system 24 transmits control signals via a cable 28 to an aroma-release system 30 containing at least one of the aroma release chambers 18. Based on the aroma information, at least one of the aroma release chambers 18 is actuated in response to the control signals transmitted by the computer system 24 to generate a predetermined aroma or combination or aromas.

Figure 3:
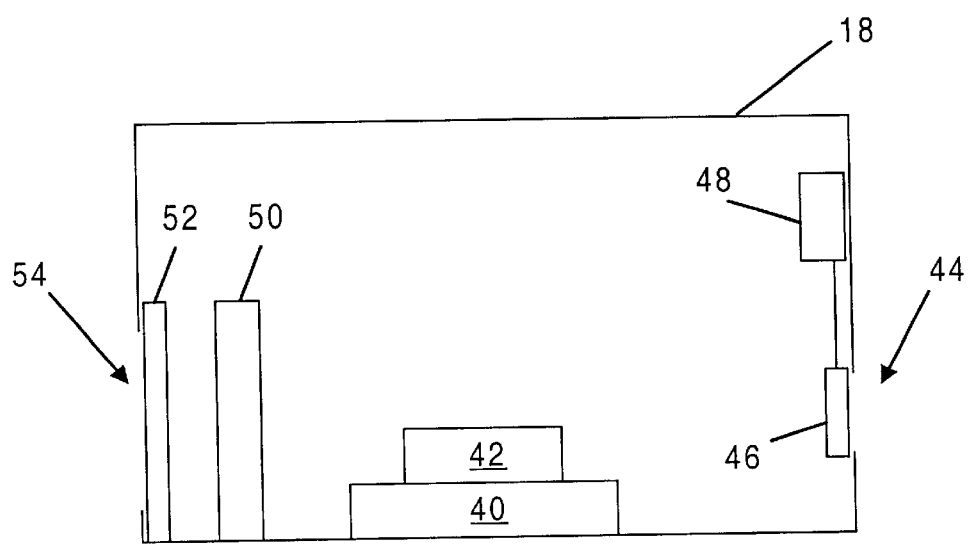
FIG. 3 is a side cross-sectional view of an aroma release chamber in accordance with a preferred embodiment of the present invention.

A side cross-sectional view of an aroma release chamber 18 in accordance with a preferred embodiment of the present invention is illustrated in FIG. 3. The aroma release chamber 18 includes a selectively controlled hot plate 40 which operates in response to control signals provided by the computer system 24 over the cable 28. A replaceable aroma stick 42 that emits a particular aroma when heated, or other type of solid, liquid, or gaseous heat actuated aroma source, is located within the aroma release chamber 18. Preferably, the aroma stick 42 is positioned directly on the hot plate 40.

The aroma release chamber 18 further includes an opening 44 covered by a door 46. An electromagnet 48 operates in response to control signals provided by the computer system 24 via the cable 28 to selectively open or close the door 46. Preferably, the door 46 is biased toward a closed position by a spring or other biasing means (not shown). A fan 50 is provided to displace a stream of air through the aroma release chamber 18 and out of the opening 44 to release the aroma generated when the aroma stick 42 is heated by the hot plate 40.

An air filtration system 52 is located over an air intake opening 54 to filter the stream of air being drawn into the aroma release chamber 18 by the fan 50. The air filtration system 52 is provided to remove previously emitted aromas from the stream of air being drawn into the aroma release chamber 18 to allow precise control of the aroma subsequently emitted by the chamber 18.

In operation, the computer system 24 retrieves and processes at least a portion of the aroma information encoded on the compact disc 22. The computer system 24 then transmits control signals to one or more predetermined aroma release chambers 18 over the cable 28 to generate the aroma or combination of aromas defined by the aroma information. Upon receipt of the control signals, the hot plate 40, the electromagnet 48 that opens the door 46, and the fan 50 in each of the predetermined aroma release chambers 18 are activated, thereby releasing the desired aroma or combination of aromas. The predetermined aroma release chambers 18 may each be activated for an identical period of time, or for different lengths of time to release different strengths of their respective aromas. Each of the predetermined aroma release chambers 18 is deactivated in response to control signals transmitted by the computer system 24 to prevent any further aroma release. When deactivated, the hot plate 40, fan 50, and electromagnet 48 are turned off, and the door 46 seals the opening 44 in the aroma release chamber 18. This process is repeated, as necessary, according to the aroma information encoded on the compact disc 22.

The foregoing description of the present invention has been presented for purposes of illustration and description. It is not intended to be exhaustive or to limit the invention to the precise form disclosed, and many modifications and variations are possible in light of the above teaching. For example, several aroma sticks, each corresponding to a different aroma, may be located within the same aroma release chamber. In this manner, a combination of aromas may be produced using a single aroma release chamber. Further, the aroma stick and hot plate in each aroma release chamber may be replaced with a solid, liquid, or gaseous, non-heat actuated aroma source. For example, the aroma source may comprise an odorant cassette, such as that disclosed in U.S. Pat. No. 5,724,256, incorporated herein by reference. Such modifications and variations that may be apparent to a person skilled in the art are intended to be included within the scope of this invention as defined by the accompanying claims.

What is claimed is:

1. An apparatus for aroma sensory stimulation comprising:
   an aroma converter for encoding aroma information into electrical signals;
   a computer readable medium for storing the electrical signals;
   a control device for processing the electrical signals stored on the computer readable medium and for generating control signals; and
   at least one aroma release chamber, each aroma release chamber configured to selectively generate a predetermined aroma under control of the control device, each aroma release chamber comprising:
   a container having an opening;
   a door controlled by the control signals for selectively covering the opening in the container;
   an aroma element, located within the container, for emitting a predetermined aroma when heated;
   a heating system controlled by the control signals for selectively heating the aroma element;
   an air filtration system located within the container for filtering air entering the container to remove aromas previously generated by the release chamber from the air entering the container; and
   an air displacement system controlled by the control signals for selectively displacing a stream of air through the container to release the predetermined aroma.

2. An aroma producing system comprising:
   a delivery system for providing aroma signals, including a computer readable medium for storing the aroma signals;
   a retrieval system for receiving and processing the aroma signals stored on the computer readable medium and for generating control signals in response to the aroma signals; and
   at least one aroma release chamber, each aroma release chamber configured to selectively generate a predetermined aroma under control of the retrieval system, each aroma release chamber comprising:
   a container having an opening;
   a door controlled by the control signals for selectively covering the opening in the container;
   an aroma source located in the container for producing a predetermined aroma;
   an air filtration system located within the container for filtering air entering the container to remove aromas previously generated from the air entering the container; and
   an air displacement system controlled by the control signals for selectively displacing a stream of air through the container to release the predetermined aroma.

3. A method for providing aroma sensory stimulation comprising:

encoding aroma information into electrical signals;
generating control signals based on the electrical signals;
providing an aroma release chamber including a container having an opening, an aroma element, located within the container, for emitting a predetermined aroma when heated, and a door;
selectively covering the opening in the container with the door in response to the control signals;
selectively heating the aroma element, using a heating system, in response to the control signals;
filtering, within the container, air entering the container to remove aromas previously generated by the aroma release chamber; and
selectively displacing a stream of air through the container in response to the control signals to release the predetermined aroma.

4. The method of claim 3, further including the step of:
storing the electrical signals produced during the encoding step.

5. The method of claim 4, wherein the electrical signals are stored on a computer readable medium.

6. The method of claim 5, wherein the computer readable medium comprises a compact disc.

7. The method of claim 4, further including the steps of:
retrieving the electrical signals stored during the storing step; and
providing the retrieved electrical signals to a control device, wherein the control device generates the control signals.

8. The method of claim 7, wherein the control device comprises a multimedia device.

9. The method of claim 3, further including the steps of:
providing a plurality of the aroma release chambers, each aroma release chamber containing an aroma element for emitting a predetermined aroma when heated.

10. The method according to claim 9, further including the steps of:
selecting at least two of the plurality of aroma chambers;
heating the aroma element in each of the selected aroma chambers; and
displacing a stream of air through each of the selected aroma chambers to release a combination of aromas.

11. The method according to claim 3, wherein the heating system comprises a hot plate.

12. The method according to claim 3, further including the step of:
biasing the door toward a closed position over the opening.

13. The method according to claim 3, further including the step of:
adjusting a strength of the emitted aroma by varying a length of time during which the stream of air is displaced through the container.

14. An apparatus comprising:
an aroma converter for encoding aroma information into electrical signals;
a control device for receiving the electrical signals and for generating control signals in response to the electrical signals; and
at least one aroma release chamber for selectively generating a predetermined aroma in response to the control signals, each aroma release chamber comprising:
a container having an opening;
a door for selectively covering the opening in the container;
an aroma element, located within the container, for emitting a predetermined aroma when heated;
a heating system for selectively heating the aroma element;
an air filtration system located within the container for filtering air entering the container to remove aromas previously generated by the aroma release chamber from the air entering the container; and
an air displacement system for selectively displacing a stream of air through the container to release the predetermined aroma.

15. The apparatus according to claim 14, wherein the electrical signals are in an analog format.

16. The apparatus according to claim 14, wherein the electrical signals are in a digital format.

17. The apparatus according to claim 14, wherein the electrical signals utilize distinct voltage levels for each aroma.

18. The apparatus according to claim 14, wherein the electrical signals are stored in a storage system.

19. The apparatus according to claim 18, wherein the electrical signals are stored on a computer readable medium.

20. The apparatus according to claim 14, further including:
a system for transferring the electrical signals from the aroma converter to the control device.

21. The apparatus according to claim 20, wherein the transferring system is selected from the group consisting of: computer readable media, radio signals, television signals, satellite signals, telephone signals, cable television signals, a computer network, and the Internet.

22. The apparatus according to claim 14, wherein each aroma release chamber further includes an electromagnetic door release.

23. The apparatus according to claim 14, wherein each aroma release chamber further includes a system for biasing the door in a closed position over the opening.

24. The apparatus according to claim 14, wherein a plurality of aroma elements are contained in at least one of the aroma release chambers.

25. The apparatus according to claim 14, wherein the heating system comprises a hot plate.

26. The apparatus according to claim 14, wherein the air displacement system includes at least one selectively controlled blower motor.

27. The apparatus according to claim 14, wherein the control system is selected from the group consisting of: a personal computer, a computer peripheral, a video game system, a television set, a home entertainment/theater system, and a stand alone module.

28. A method for providing aroma sensory stimulation comprising:
encoding aroma information into electrical signals;
generating control signals based on the electrical signals;
providing an aroma release unit including at least one aroma element for emitting a predetermined aroma;
selectively stimulating at least one aroma element in response to the control signals to release at least one predetermined aroma; and
selectively dispensing the at least one predetermined aroma in response to the control signals.

29. The method of claim 28, further including the step of:
storing the electrical signals produced during the encoding step.

30. The method of claim 29, wherein the electrical signals are stored on a computer readable medium.

31. The method of claim 30, wherein the computer readable medium comprises a compact disc.

32. The method of claim 29, further including the steps of:
   retrieving the electrical signals stored during the storing step; and
   providing the retrieved electrical signals to a control device, wherein the control device generates the control signals.

33. The method of claim 32, wherein the control device comprises a multimedia device.

34. The method of claim 28, further including the steps of:
   providing a plurality of the aroma units, each aroma unit containing at least one aroma element for emitting a predetermined aroma.

35. The method according to claim 34, further including the steps of:
   selecting at least two of the plurality of aroma units;
   stimulating the at least one aroma element in each of the selected aroma units; and
   selectively dispensing each of the predetermined aromas.

36. The method according to claim 28, wherein the electrical signals are encoded in a format selected from the group consisting of: radio signals, television signals, satellite signals, telephone signals, cable television signals, digital signals, analog signals, and Internet data.

37. The method according to claim 28, wherein the aroma release element is provided in a form selected from the group consisting of: solid, gaseous, liquid, or combinations thereof.

38. The method according to claim 28, further including the step of:
   adjusting a strength of the at least one predetermined aroma by varying a length of time during which the predetermined aroma is dispensed.

39. The method according to claim 28, wherein the method is performed in conjunction with a system selected from the group consisting of: a personal computer, a computer peripheral, a video game system, a television set, a home entertainment/theater system, and a stand-alone module.

40. The method according to claim 28, wherein the aroma element is selected from the group consisting of: a solid, a stick, an oil, a liquid, a gel, a vapor, and a gas.

41. The method according to claim 28, wherein the aroma release unit further comprises an aroma cassette.

* * * * *